United States Patent [19]
Pinzon et al.

US005728371A

[11] Patent Number: 5,728,371
[45] Date of Patent: Mar. 17, 1998

[54] SKIN PROTECTION, FRAGRANCE ENHANCING AND VITAMIN DELIVERY COMPOSITION

[75] Inventors: Carlos Pinzon, Hackensack; Paul Thau, Berkley Heights, both of N.J.

[73] Assignee: L'Oreal, S.A., Paris, France

[21] Appl. No.: 643,075

[22] Filed: Apr. 30, 1996

Related U.S. Application Data

[63] Continuation-in-part of Ser. No. 641,066, Apr. 29, 1996, abandoned.

[51] Int. Cl.$^6$ ................................ A61K 7/42; A61K 7/00
[52] U.S. Cl. ......................... 424/59; 424/60; 424/400; 424/401
[58] Field of Search ........................ 424/59, 60, 400, 424/401

[56] References Cited

U.S. PATENT DOCUMENTS

| | | | |
|---|---|---|---|
| 5,009,969 | 4/1991 | Miller | 424/59 |
| 5,169,624 | 12/1992 | Ziegler et al. | 424/59 |
| 5,318,774 | 6/1994 | Alban et al. | 424/59 |
| 5,486,352 | 1/1996 | Guerrero | 424/59 |

FOREIGN PATENT DOCUMENTS 1196868  11/1985  Canada.

*Primary Examiner*—Shelley A. Dodson
*Attorney, Agent, or Firm*—Baker & Botts, L.L.P.

[57] ABSTRACT

The present invention provides a composition for extending the longevity of the fragrance on the skin which comprises at least one fragrance composition and at least one polysaccharide alkylether which includes at least two different moieties and at least one hydroxyl group substituted with a saturated $C_1$–$C_{24}$ alkyl chain. The present invention also provides a method for extending the longevity of fragrance on the skin which involves applying to the skin a composition including at least one fragrance composition and at least one polysaccharide alkylether having at least two different moieties and at least one hydroxyl group substituted with a saturated $C_1$–$C_{24}$ alkyl chain.

22 Claims, No Drawings

SKIN PROTECTION, FRAGRANCE ENHANCING AND VITAMIN DELIVERY COMPOSITION

This is a continuation in part of Ser. No. 641,066, filed Apr. 29, 1996, now abandoned.

BACKGROUND OF THE INVENTION

This invention is directed to a composition having enhanced skin protection properties against ultraviolet rays, and a method of enhancing the skin protection properties of sunscreen compositions. This invention is also directed to a composition for extending the longevity of fragrance on the skin, and a method for extending the longevity of fragrance on the skin. This invention is also directed to an anhydrous composition for delivering one or more vitamins to the skin, and a method for delivering one or more vitamins to the skin.

The damaging effect of the sun's ultraviolet radiation on the skin is well known. Accordingly, many skin protection products have been developed which contain various materials intended to block or absorb ultraviolet rays, thereby preventing or lessening damage to the skin. Typically, such products are oil-in-water or water-in-oil emulsions and anhydrous systems containing sunscreens or ultraviolet radiation filters, and the compositions are topically applied to the skin. The relative skin protection afforded by such compositions is typically measured by means of determining a "sun protection factor" or SPF for the composition.

It is believed that there is a relationship between the rheological properties of such emulsions and the SPF of the composition. Since the skin is not a flat surface, but rather has a topography made up of irregular peaks and valleys, it is believed that the rheological properties of such emulsions (particularly the shear sensitivity of the viscosity) influence the SPF factor of such compositions. The rheological properties of an emulsion are provided, for the most part, by water soluble rheological additives such as carbomers, cellulosics, and natural and synthetic gums. The contributory rheological properties of the oil phase of the emulsion are relatively minimal. Oils typically exhibit Newtonian viscosity (i.e., non-shear sensitive), which is not very effective in covering the skin. Accordingly, the rheological properties of traditional skin protection emulsions based upon water-soluble rheological additives are greatly reduced as water evaporation from the skin takes place. The remaining oil phase provides a less effective covering of the skin, with concurrent reduction in protection from ultraviolet rays. Thus, it would be advantageous to prepare a skin protection composition which is an emulsion having enhanced SPF and which avoids the above-described problems.

It has now been found that sunscreen compositions comprising at least one polysaccharide alkylether comprising at least two different moieties and at least one hydroxyl group substituted with a saturated $C_1$–$C_{24}$ alkyl chain have enhanced SPF properties. Accordingly, it is one object of this invention to provide a composition having enhanced skin protection properties from ultraviolet radiation. It is another object of this invention to provide a method of enhancing the skin protection properties from ultraviolet radiation using such a composition. It is a feature of the composition and method of this invention that the composition contains at least one sunscreen composition and at least one oil soluble polymer which is a polysaccharide alkylether comprising at least two different moieties and at least one hydroxyl group substituted with a saturated $C_1$–$C_{24}$ alkyl chain. This invention is advantageous in that the use of the oil soluble polymer enhances the SPF capability of the skin protection composition. While not wishing to be bound by any theory, it is believed that incorporation of this oil soluble polymer into the oil phase increases viscosity and provides film forming properties that enhance SPF activity on skin.

The use of various fragrance-bearing compositions on the skin has been known for centuries. However, improving the duration of fragrances on the skin has always posed a challenge. In the past, attempts have been made to introduce various materials into fragrance compositions to achieve such results. Such materials have included polyvinyl pyrrolidone (PVP) resins, acrylic acid-based polymers and other polymeric materials. However, incompatibility of these materials with fragrance oils, the limited solubility of such polymers in the fragrance compositions, and changes in the character of the fragrance have all impaired improvement of the longevity of fragrance on the skin. Accordingly, it would be advantageous to prepare a composition capable of imparting fragrance to the skin and capable of extending the longevity of the fragrance on the skin.

It has now been found that fragrance-bearing compositions comprising at least one fragrance composition and at least one polysaccharide alkylether comprising at least two different moieties and at least one hydroxyl group substituted with a saturated $C_1$–$C_{24}$ alkyl chain are capable of extending the longevity of the fragrance to the skin. Accordingly, it is another object of this invention to provide a composition for extending the longevity of fragrance on the skin. It is another object of this invention to provide a method of extending the longevity of fragrance on the skin using such a composition. It is a feature of the composition and method of this invention that the composition contains at least one fragrance composition and at least one oil soluble polymer which is an ethylated galactomannan. This invention is advantageous in that the use of the polysaccharide alkylether oil soluble polymer extends the longevity of fragrance imparted to the skin by the fragrance composition.

The delivery of various vitamins to the skin is known to be beneficial. For example, vitamin C (i.e., ascorbic acid) and vitamin E (i.e., tocopherol) are well known skin care ingredients with proven beneficial free radical scavenger and antioxidant properties. However, to be effective these and other vitamins must be delivered to the skin in the active form. For example, vitamin E is oil soluble, but vitamin C is water soluble and is very unstable in water, degrading very rapidly. Thus, effective delivery of vitamin C to the skin in an aqueous system is very difficult to achieve. Accordingly, the use of anhydrous or essentially anhydrous systems to deliver effective amounts of vitamin C to the skin have been attempted. Such systems have employed materials such as petrolatum, waxes, fatty alcohols, fatty acids, polyethylenes and low HLB emulsifiers. However, such systems have not proven to be entirely adequate in terms of cosmetic application properties. In addition, such systems have exhibited marginal to unacceptable stability, with loss or degradation of rheological properties. Thus, it would be advantageous to prepare an anhydrous composition capable of delivering one or more vitamins to the skin which has good stability and cosmetic application properties.

It has now been found that anhydrous compositions comprising at least one vitamin and at least one polysaccharide alkylether comprising at least two different moieties and at least one hydroxyl group substituted with a saturated $C_1$–$C_{24}$ alkyl chain are capable of delivering the vitamin, including combinations of vitamins C and E, to the skin. Accordingly, it is yet another object of this invention to provide an anhydrous composition for delivering one or more vitamins to the skin. It is another object of this invention to provide a method for delivering one or more vitamins to the skin using such a composition. It is a feature of the composition and method of this invention that the composition contains at least one vitamin and at least one oil soluble polymer which is a polysaccharide alkylether comprising at least two different moieties and at least one hydroxyl group substituted with a saturated $C_1$-$C_{24}$ alkyl chain. This invention is advantageous in that the use of the polysaccharide alkylether oil soluble polymer provides a stable, cosmetically acceptable vehicle for delivery of vitamins to the skin.

SUMMARY OF THE INVENTION

A composition for having enhanced skin protection from ultraviolet rays comprises at least one sunscreen composition and at least one polysaccharide alkylether comprising at least two different moieties and at least one hydroxyl group substituted with a saturated $C_1$-$C_{24}$ alkyl chain. The sunscreen composition comprises one or more materials capable of filtering, blocking or absorbing ultraviolet rays. A method for enhancing the skin protection properties of sunscreen formulations against ultraviolet rays comprises applying to the skin a composition comprising at least one sunscreen composition and at least one polysaccharide alkylether comprising at least two different moieties and at least one hydroxyl group substituted with a saturated $C_1$-$C_{24}$ alkyl chain.

A composition for extending the longevity of fragrance on the skin comprises at least one fragrance composition and at least one polysaccharide alkylether comprising at least two different moieties and at least one hydroxyl group substituted with a saturated $C_1$-$C_{24}$ alkyl chain. The fragrance composition comprises one or more materials having a fragrant odor. A method for extending the longevity of fragrance on the skin comprises applying to the skin a composition comprising at least one fragrance composition and at least one polysaccharide alkylether comprising at least two different moieties and at least one hydroxyl group substituted with a saturated $C_1$-$C_{24}$ alkyl chain.

An anhydrous composition for delivering one or more vitamins to the skin comprises at least one vitamin and at least one polysaccharide alkylether comprising at least two different moieties and at least one hydroxyl group substituted with a saturated $C_1$-$C_{24}$ alkyl chain. The composition for delivering vitamins to the skin comprises at least one vitamin. For example, the composition may comprise vitamin C, vitamin E, or a combination thereof. A method for delivering one or more vitamins to the skin comprises applying to the skin a composition comprising at least one vitamin and at least one polysaccharide alkylether comprising at least two different moieties and at least one hydroxyl group substituted with a saturated $C_1$-$C_{24}$ alkyl chain.

All of these compositions are most preferably topically applied to the skin. The polysaccharide alkyl ether has a weight average molecular weight in the range of 1 to 1,000,000, preferably 1 to 500,000, more preferably greater than 100,000, most preferably greater than 200,000. The polysaccharide alkylether moieties are preferably selected from the mannose, galactose, glucose, fructose, faranose, rhamnose and arabinose. The number of substituted hydroxyl groups is preferably 1-6, most preferably 2-4, the saturated hydrocarbon alkyl chain is preferably $C_1$-$C_{10}$, most preferably $C_1$-$C_3$. For example, the hydrocarbon alkyl chain may be straight or branched and may include, but is not limited to, methyl, ethyl, n-propyl, isopropyl, n-butyl, isobutyl, t-butyl. In a particularly preferred embodiment, the polysaccharide alkylether is an ethylated galactomannan preferably having a high degree of substitution, for example a degree of substitution of about 2.0 or greater, preferably 2.5 or greater, such as ethylated guar having a degree of ethyl substitution of about 2.5 or greater.

DETAILED DESCRIPTION OF THE PREFERRED EMBODIMENTS

The skin-protection enhancing composition of this invention comprises at least one sunscreen composition and at least one oil soluble polymer which is a polysaccharide alkylether comprising at least two different moieties and at least one hydroxyl group substituted by a saturated hydrocarbon alkyl chain having 1 to 24 carbon atoms.

The sunscreen composition may be any composition or compositions which absorb, block or otherwise mitigate ultraviolet radiation. Without wishing to limit the invention in any way, such sunscreen compositions include, but are not limited to, p-aminobenzoic acid, 2-ethoxyethyl-p-methoxy cinnamate, diethanolamine-p-methoxy cinnamate, digalloyl trioleate, 2,2-dihydroxy-4-methoxybenzophenone, ethyl-4-bis-(hydroxypropyl)aminobenzoate, 2-ethylhexyl-2-cyano-3,3-diphenyl acrylate, ethylhexyl-p-methoxy cinnamate, 2-ethylhexyl salicylate, glyceryl aminobenzoate, 3,3,5-trimethylcyclohexyl salicylate, lawsone with dihydroxyacetone, menthyl anthranilate, 2-hydroxy-4-methoxy benzophenone, amyl-p-dimethylamino benzoate, 2-ethylhexyl-p-dimethylamino benzoate, 2-phenylbenzimidazole-5-sulphonic acid, red petrolatum, 2-hydroxy-4-methoxybenzophenone-5-sulphonic acid, titanium dioxide, triethanolamine salicylate, and the like. In addition, suitable sunscreens for use in the sunscreen composition are set forth in Sunscreens Monogram, Federal Register, Vol. 58, No. 90, Proposed Rules, p. 28295 (May 12, 1993) Subpart B. Preferred sunscreen compositions include benzophenone-3, octyl methoxycinnamate (OMC) and combinations thereof. Commercial examples of sunscreen compositions which may be employed include NEO HELIOPAN AV, an OMC composition manufactured by Haarmann and Reimer or Parsol MCX, manufactured by Givaudan, and UVINUL M-40, a benzophenone-3 product manufactured by BASF. The sunscreen composition is employed in the skin-protection enhancing composition in a concentration range approved by the United States Food and Drug Administration (FDA). A sunscreen such as OMC is employed in a concentration range of 2 to 7.5 weight percent, based on the total weight of the skin protection formulation. Benzophenone-3 is employed in a concentration range of 2 to 6, preferably 2 to 3 weight percent, based on the total weight of the skin protection formulation.

The polysaccharide alkylether comprises at least two different moieties selected from the group consisting of guar (i.e., galactomannan), karaya, locust bean, and tragacanth, preferably guar. At least one hydroxyl group, preferably 1 to 6 hydroxyl groups, most preferably 2 to 4 hydroxyl groups in the polysaccharide alkylether are substituted with a saturated hydrocarbon alkyl chain having 1 to 24 carbon atoms, preferably 1 to 10 carbon atoms, most preferably 1 to 3 carbon atoms.

In a particularly preferred embodiment the polysaccharide alkylether is an ethylated galactomannan such as an ethylated guar having an ethyl degree of substitution (DS) of about 2.0 or greater, most preferably about 2.5 or greater. A particularly preferred ethylated galactomannan for use in the present invention is commercially available from Hercules Inc. under the AQUALON trade name, most preferably AQUALON AQU-D-3360-L and AQU-3360-H. The polysaccharide alkylether is employed in the enhanced skin protection composition in a concentration range of about 0.5 to 10 weight percent, based upon the total weight of the skin protection formulation. The invention may be employed in an anhydrous sun protection formulation as well as in oil-in-water or water-in-oil emulsion type sun protection formulations.

Other conventional additives typically employed in sun protection formulations may be employed in conjunction with the present invention. Such additives include, but are not limited to, solvents, emollients, solubilizers, cosmetic bases, defatters, plasticizers, lubricants, deoilers, thickeners, stabilizers, additional occlusive barriers, viscosifiers, emulsifiers, surfactants, film formers, water proofing additives, moisturizers, botanical extracts, fillers, preservatives, ultraviolet radiation filters and the like, as are well known to those skilled in the art of sunscreen formulations.

The following examples illustrate various preferred embodiments of the enhanced skin protection composition of this invention. It will be understood that the following examples are illustrative and are not meant to limit the invention in any way. All of the formulations were analyzed for in-vitro SPF values using an SPF-290 analyzer manufactured by the Optometrics Corporation. Viscosity was measured for one minute at 22.7° C. using a Brookfield DV-II+, RV type viscometer, with a T-C bar, speed 5 rpm. Formula D was prepared (thickened) with silica (Cabosil M5) as an additional control sample.

EXAMPLE 1

Anhydrous Sunscreen Preparation

| Ingredients | FORMULAS A | B | D |
|---|---|---|---|
| Finsolv TN (C$_{12}$-C$_{15}$ alkyl benzoate) | 87.50 | 79.50 | 81.50 |
| Benzophenone-3 | 5.00 | 5.00 | 5.00 |
| OMC | 7.50 | 7.50 | 7.50 |
| AQU-D-3360-H | — | 8.00 | — |
| Cabosil M5 | — | — | 6.00 |
| TOTALS | 100.00 | 100.00 | 100.00 |
| In Vitro SPF | 10.00 | 19.90 | 16.00 |

The ingredients were heated moderately (45° C. to 60° C.) to properly dissolve Benzophenone-3 and mixed together using a propeller mixer. With respect to formula B, Finsolv TN was heated to 75° C. and AQU-D-3360-H was dispersed therein using a propeller mixer. The other ingredients were then added sequentially using a propeller mixer.

EXAMPLE 2

Oil in Water Emulsion including organic UV-A and UV-B filters

| Phase | Ingredients | FORMULAS A WT % | B WT % |
|---|---|---|---|
| A | Water | 62.75 | 64.85 |
| A | Pemulen TR-1 | 0.10 | 0.10 |
| A | Glycerine | 2.50 | 2.50 |
| A | Glucam E-20 | 2.50 | 2.50 |
| A | No. 2 EDTA | 0.05 | 0.05 |
| B | O.M.C. | 7.50 | 7.50 |
| B | Benzophenone-3 | 5.00 | 5.00 |
| B | AQU-3360-H | 2.00 | — |
| B | Finsolv TN | 8.50 | 8.50 |
| B | Arlacel 165 | 3.00 | 3.00 |
| B | Cetyl Alcohol | 1.00 | 1.00 |
| C | Triethanolamine | 0.10 | 0.10 |
| C | Water | 1.00 | 1.00 |
| D | Cyclomethicone | 3.00 | 3.00 |
| E | Germaben II | 1.00 | 1.00 |
|  |  | 100.00 | 100.00 |
| In Vitro SPF |  | 13.60 | 6.00 |

Phase A was prepared by mixing together the ingredients using a propeller mixer and heating at 75° C. Phase B, the oil phase, was prepared as follows. Finsolv TN, OMC and Benzophenone were blended together and heated to 75° C. to 85° C. AQU-3360-H was then added to this blend while rapidly agitating with a propeller mixer. After the AQU-3360-H was incorporated completely into the mixture, i.e., no more particles were visible and the mixture appeared to be a clear solution, the remaining Phase B ingredients were added. Phase B was then added to Phase A with rapid agitation at a temperature of 75° C. Phase C was then added to this mixture of Phase A and Phase B and the resulting mixture was cooled to below 48°–50° C. Phase D and Phase E were then added to this mixture. Pemulen TR-1 is a C$_{10-30}$ alkyl acrylate crosspolymer available from B.F. Goodrich. Glucam E-20, available from Amerchol, a polyethylene glycol ether of methyl glucose that has an average of 20 ethoxy groups. Arlacel 165, available from ICI America, is a polyethylene glycol ester of stearic acid that has an average of 100 ethoxy groups. Germaben II is a preservative available from Sutton.

EXAMPLE 3

Water in Oil Emulsion with micronized TiO$_2$ UV filter

| Phase | Ingredients | FORMULAS A WT % | B WT % |
|---|---|---|---|
| A | Abil-EM-90 | 2.50 | 2.50 |
| A | AQU-D-3360-H | 0.40 | — |
| A | Capric Caprylic Triglyceride | 2.50 | 2.50 |
| A | D.C. 556 Fluid | 4.60 | 5.00 |
| A | Isopropyl Myristate | 6.00 | 6.00 |
| A | Polysynlane | 2.50 | 2.50 |
| A | Silkflo 362 | 3.25 | 3.25 |
| A | ON-60-TA (60%) | 8.50 | 8.50 |
| B | D.I. Water | 64.75 | 64.75 |
| B | Glycerine | 3.50 | 3.50 |

Water in Oil Emulsion with micronized TiO₂ UV filter

| Phase | Ingredients | FORMULAS A WT % | B WT % |
|---|---|---|---|
| B | NaCl | 0.50 | 0.50 |
| B | Germaben II | 1.00 | 1.00 |
| | | 100.00 | 100.00 |
| Viscosity (cps) | | 73,000 | 68,000 |
| In Vitro SPF | | 16.20 | 13.90 |

AQU-D-3360-H was predispersed in D.C. 556 fluid at a temperature of 75° C. After cooling to room temperature the dispersion was added to the other Phase A ingredients and the mixture stirred using a propeller mixer. Phase B was prepared and slowly added to Phase A while stirring with a propeller mixture. Abil-EM-90, available from Goldschmidt, is acetyl dimethicone copolyol. Polysynlane is a hydrogenated polyisobutene available from Nippon Oil and Fats. D.C. 556 fluid is phenyl trimethicone. Silkflo is a polydecene. ON-60-TA (60%), available from Kobo, is a mixture of 60% micronized TiO₂ in octyldodecyl neopentanoate.

EXAMPLE 4

Water in Oil Emulsion including organic UV-A and UV-B filters

| Phase | Ingredients | FORMULAS A WT % | B WT % |
|---|---|---|---|
| A | Abil-EM-90 | 2.50 | 2.50 |
| A | Finsolv TN | 11.50 | 12.50 |
| A | AQU-3360-H | 1.00 | — |
| A | OMC | 7.50 | 7.50 |
| A | Benzophenone-3 | 5.00 | 5.00 |
| A | Capric/Caprylic Triglyceride | 1.75 | 1.75 |
| A | Isopropyl Myristate | 3.00 | 3.00 |
| A | Polysynlane | 1.00 | 1.00 |
| A | Cyclomethicone | 2.50 | 2.50 |
| B | Water | 59.25 | 59.25 |
| B | Glycerine | 3.50 | 3.50 |
| B | NaCl | 0.50 | 0.50 |
| B | Germaben II | 1.00 | 1.00 |
| | | 100.00 | 100.00 |
| Viscosity (cps) | | 27,000 | 32,000 |
| In Vitro SPF | | 23.30 | 18.70 |

AQU-3360-H was predispersed in Finsolv TN at a temperature of 75° C. After cooling to room temperature, the dispersion was adding to the other Phase A ingredients, and the mixture stirred using a propeller mixer. Phase B was prepared and slowly added to Phase A while stirring with a propeller mixture. Both formula A and B exhibited satisfactory stability both at 25° and 45° C.

As set forth above, the in-vitro SPF results indicate that the invention has enhanced sun protection (SPF) properties.

Without being bound by any one theory, it is expected that use of the polysaccharide alkylether oil soluble polymer in the skin protection composition of this invention enables the oil-soluble ultraviolet filter or sunscreen material contained in the composition to be distributed more uniformly on the skin topography. It is also expected that the rheological properties are improved and made more flexible with respect to oil phases of the composition that have previously been thickened by waxes, polyethylenes and long chain hydrocarbons and the like also contained within the composition. It is also expected that use of the polysaccharide alkylether prolongs the activity of the sunscreen composition on the skin, and reduces the penetration of oil-soluble sunscreen composition into the skin, thereby lowering the potential of skin irritation due to such penetration. It is also expected that use of the polysaccharide alkylether will enable the level or concentration of the sunscreen or ultraviolet radiation filter material to be reduced in the skin protection composition, thereby reducing the cost and possible harmful side effects of such materials. It is also expected that use of the polysaccharide alkylether will impart improved water-resistant properties to the skin-protection composition, thereby enhancing its use at the beach, pools, while swimming and the like.

The fragrance-extending composition embodiment of this invention comprises at least one fragrance composition and at least one oil soluble polymer which is a polysaccharide alkylether comprising at least two different moieties and at least one hydroxyl group substituted by a saturated hydrocarbon alkyl chain having 1 to 24 carbon atoms. The polysaccharide alkylether employed in the fragrance extending composition of this invention is as described above with respect to the enhanced skin protection composition embodiment of this invention. The absence of any chemical odor in the oil soluble and lipophilic polymer makes its use particularly suitable in fragrance and perfume compositions. The oil soluble polymer may be present in the fragrance enhanced composition of this invention in a concentration range of about 0.1 to 10 weight percent, preferably 0.5 to 10 weight percent, based upon the total formulation weight of the fragrance enhanced composition.

The fragrance-extending composition also comprises at least one composition or compositions which impart fragrance. Without wishing to limit the invention in any way, such fragrance compositions include oils, perfumes and the like, as well as combinations thereof, as are well known to those skilled in the art. The fragrance is present in a concentration range of 1 to 99.5% weight percent, based upon the total formulation weight of the fragrance enhanced composition.

The following examples illustrate various preferred embodiments of the fragrance extended composition of this invention. It will be understood that the following examples are illustrative and are not meant to limit the invention in any way. The formulations were evaluated for fragrance duration.

EXAMPLE 5

| Ingredient | D Wt. % | E Wt. % |
|---|---|---|
| AQU-D-3360-H | 2.00 | — |
| Ethyl Alcohol | 68.00 | 70.00 |
| Deionized Water | 18.00 | 18.00 |
| GIO EDT Oil | 12.00 | 12.00 |
| | 100.00 | 100.00 |

GIO EDT oil is the fragrance oil used in GIO eau de toilette, a commercial product. The formulations were evaluated for fragrance duration. Formula D prepared in accordance with the invention was found to exhibit significantly longer fragrance duration on the skin as compared with control formula E.

EXAMPLE 6

|  | A | B |
| --- | --- | --- |
| Polo Sport for Woman EDT | 100.00 | 97.00 |
| AQU-D-3360-L | — | 3.00 |
|  | 100.00 | 100.00 |

In Example 6, a commercial fragrance-bearing formulation A (POLO SPORT FOR WOMEN eau de toilette) was evaluated for fragrance duration, and compared with formulation B, in which the oil soluble polymer AQU-D-3360-L was added. Preliminary evaluation tests confirmed that formulation B prepared in accordance with the invention exhibited significantly longer fragrance duration on the skin.

Without being bound by any one theory, it is expected that use of the polysaccharide alkylether oil soluble polymer in the fragrance-extending composition of this invention enables the uniformity of fragrance rendition in fragrance and perfume vehicles to be enhanced. It is also expected that this invention will lower the irritation and sensitization problems which are sometimes experienced with some fragrance and perfume systems.

The anhydrous vitamin-delivery composition of this invention comprises at least one vitamin and at least one oil soluble polymer which is a polysaccharide alkylether comprising at least two different moieties and at least one hydroxyl group substituted by a saturated hydrocarbon alkyl chain having 1 to 24 carbon atoms. The polysaccharide alkylether employed in the vitamin delivery composition embodiment of this invention is as described above with respect to the enhanced skin protection composition and fragrance-enhancing embodiments of this invention. The oil soluble polymer may be present in the vitamin-delivery composition embodiment of this invention in a concentration range of about 0.5 to 10 weight percent, based upon the total formulation weight.

Vitamins which may be employed in this embodiment of the invention include, but not limited to, vitamin A, pro vitamin A, vitamin $B_1$, vitamin $B_2$, vitamin $B_3$, vitamin $B_4$, vitamin $B_5$, vitamin $B_6$, vitamin $B_{12}$, vitamin C, vitamin D, vitamin $D_2$, vitamin $D_3$, vitamin E, vitamin F, vitamin $K_1$ and combinations and derivatives thereof. Preferred vitamins include vitamins C and E, as well as derivatives and combinations thereof. In a particularly preferred embodiment, the invention comprises both vitamin C and vitamin E. The vitamins may be present in a concentration from about 0.5–50 percent by weight, preferably 0.5–10 percent by weight, based upon the total weight of the composition.

The vitamin delivery composition embodiment also comprises at least one composition or compositions which are typically employed in conjunction with vitamin-containing compositions. Without wishing to limit the invention in any way, such vitamin-containing compositions include solvents, emulsifiers, solubilizers and the like, as well as combinations thereof, as are well known to those skilled in the art.

The following examples illustrate various preferred embodiments of the vitamin-delivery composition of this invention. It will be understood that the following examples are illustrative and are not meant to limit the invention in any way. The formulations were evaluated for stability over time under elevated temperature conditions (45 degrees C.) for six weeks, with satisfactory results.

EXAMPLE 7

| Vitamin C Suspension | | |
| --- | --- | --- |
| Phase | Ingredients | % Wt |
| A | Eutanol G | 87.40 |
| A | AQU-D-3360-H | 7.60 |
| B | Micronized Ascorbic Acid | 5.00 |
|  | Total | 100.00 |
| Viscosity (cps) | — | 83,000 |

Eutanol G, available from Henkel, is an octyldodecanol. AQU-D-3360-H was predispersed in Eutanol G. Micronized ascorbic acid was added to the dispersion while stirring with a propeller mixture.

EXAMPLE 8

| Vitamin C and E Suspension | | | |
| --- | --- | --- | --- |
| Phase | Ingredients | A Wt. % | B Wt. % |
| A | Finsolv TN | 64.50 | 41.00 |
| A | Tocopherol | 1.00 | 1.00 |
| A | Wickenol 151 | — | 10.00 |
| A | Cyclomethicone | 21.50 | 35.00 |
| B | AQU-D-3360-H | 8.00 | 8.00 |
| C | Vitamin C | 5.00 | 5.00 |
|  | TOTAL | 100.00 | 100.00 |
| Viscosity (cps) | — | 99,000 | 92,000 |

Wickenol 151 is an isononyl isononanoate available from CasChem. The components of Phase A were mixed together with a propeller mixer. AQU-D-3360-H was added to the other Phase A ingredients while stirring with a propeller mixture. Vitamin C was added to the resulting mixture while stirring with a propeller mixer.

Without wishing to be bound by any one theory, it is believed that the present vitamin-delivery composition and method embodiments of the present invention are advantageous in that the composition maintains satisfactory rheological properties at both elevated and room temperature conditions. It is also believed that rheological properties of the final vitamin suspension of the invention may advantageously be tailored by adjusting gum levels to change viscosity. Moreover, because the oil soluble polymer component has water absorption properties, the bioavailability of the vitamin or vitamins is enhanced upon application of the vitamin suspension to the skin.

Although this invention has been illustrated by reference to specific embodiments, it will be apparent to those skilled in the art that various changes and modifications may be made which clearly fall within the scope of this invention.

The invention claimed is:

1. A composition for extending the longevity of fragrance on the skin comprising at least one fragrance composition and at least one polysaccharide alkylether comprising at least two different moieties and at least one hydroxyl group substituted with a saturated $C_1$–$C_{24}$ alkyl chain.

2. A composition according to claim 1, wherein the moieties are selected from the group consisting of mannose, galactose, glucose, furanose, rhamnose and arabinose.

3. A composition according to claim 1, wherein the number of substituted hydroxyl groups is 1–6.

4. A composition according to claim 3, wherein the number of substituted hydroxyl groups is 2–4.

5. A composition according to claim 3, wherein the saturated alkyl chain has a length of $C_1$–$C_{10}$.

6. A composition according to claim 5, wherein the saturated alkyl chain has a length of $C_1$–$C_3$.

7. A composition according to claim 1, wherein the polysaccharide alkylether is selected from the group consisting of guar, karaya, locust bean, and tragacanth.

8. A composition according to claim 1, wherein the polysaccharide alkylether is ethylated galactomannan having a degree of substitution of about 2.0 or greater.

9. A composition according to claim 8, wherein the ethylated galactomannan has a degree of substitution of about 2.5 or greater.

10. A composition according to claim 1, wherein the ethylated galactomannan is an ethylated guar.

11. A composition according to claim 10, wherein the ethylated guar has an ethyl degree of substitution of about 2.5 or greater.

12. A method for extending the longevity of fragrance on the skin comprising applying to the skin a composition comprising at least one fragrance composition and at least one polysaccharide alkylether comprising at least two different moieties and at least one hydroxyl group substituted with a saturated $C_1$–$C_{24}$ alkyl chain.

13. A method according to claim 12, wherein the moieties are selected from the group consisting of mannose, galactose, glucose, furanose, rhamnose and arabinose.

14. A method according to claim 12, wherein the number of substituted hydroxyl groups is 1–6.

15. A method according to claim 14, wherein the number of substituted hydroxyl groups is 2–4.

16. A method according to claim 12, wherein the saturated alkyl chain has a length of $C_1$–$C_{10}$.

17. A method according to claim 16, wherein the saturated alkyl chain has a length of $C_1$–$C_3$.

18. A method according to claim 12, wherein the polysaccharide alkylether is selected from the group consisting of guar, karaya, locust bean, and tragacanth.

19. A method according to claim 12, wherein the polysaccharide alkylether is an ethylated galactomannan having a degree of substitution of about 2.0 or greater.

20. A method according to claim 19, wherein the ethylated galactomannan has a degree of substitution of about 2.5 or greater.

21. A method according to claim 12, wherein the ethylated galactomannan is an ethylated guar.

22. A method according to claim 21, wherein the ethylated guar has an ethyl degree of substitution of about 2.5 or greater.

* * * * *

UNITED STATES PATENT AND TRADEMARK OFFICE
CERTIFICATE OF CORRECTION

PATENT NO. : 5,728,371

DATED : March 17, 1998

INVENTOR(S) : Pinzon et al.

It is certified that error appears in the above-indentified patent and that said Letters Patent is hereby corrected as shown below:

<u>First page, after last line of Item 56</u>, insert --OTHER DOCUMENTS
Majewicz et al., Research Disclosure RD37807, October 10, 1995.
Haag et al., Research Disclosure RD37816, October 10, 1995.
"AQU D3360 Modified Polysaccharide Oil Soluble Polymer (OSP)" by Aqualon.--.

<u>Col. 7, line 25</u>, "Silkflo" should read --Silkflo 362--;

<u>Col. 7, line 58</u>, "adding" should read --added--;

<u>Col. 7, line 61</u>, "mixture" should read --mixer--;

<u>Col. 10, line 46</u>, "mixture" should read --mixer--.

Signed and Sealed this

Seventh Day of July, 1998

Attest:

*Attesting Officer*

BRUCE LEHMAN

*Commissioner of Patents and Trademarks*